(12) United States Patent
Kriveshko et al.

(10) Patent No.: US 9,191,648 B2
(45) Date of Patent: Nov. 17, 2015

(54) HYBRID STITCHING

(75) Inventors: Ilya A. Kriveshko, Littleton, MA (US); Benjamin Frantzdale, Shrewsbury, MA (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 323 days.

(21) Appl. No.: 14/000,442

(22) PCT Filed: Feb. 17, 2012

(86) PCT No.: PCT/US2012/025554
§ 371 (c)(1),
(2), (4) Date: Aug. 20, 2013

(87) PCT Pub. No.: WO2012/115863
PCT Pub. Date: Aug. 30, 2012

(65) Prior Publication Data
US 2013/0329020 A1 Dec. 12, 2013

Related U.S. Application Data

(60) Provisional application No. 61/445,464, filed on Feb. 22, 2011.

(51) Int. Cl.
*H04N 13/02* (2006.01)
*A61B 1/00* (2006.01)
(Continued)

(52) U.S. Cl.
CPC .......... *H04N 13/0203* (2013.01); *A61B 1/0005* (2013.01); *A61B 1/00009* (2013.01);
(Continued)

(58) Field of Classification Search
CPC ................... G06T 2207/30036; G06T 7/0024; G06T 19/00; G06T 2207/20072; G06T 2207/10028; A61B 1/24; A61B 1/00009; A61B 1/00193; A61B 1/00039; A61B 1/0005; H04N 13/0203
USPC ........................................................... 348/50
See application file for complete search history.

(56) References Cited

U.S. PATENT DOCUMENTS

| 5,410,614 A | 4/1995 | Chou |
| 6,128,086 A | 10/2000 | Fowler |

(Continued)

FOREIGN PATENT DOCUMENTS

| CN | 101799293 | 8/2010 |
| WO | 2007-084589 | 7/2007 |
| WO | 2012-115862 | 8/2012 |

OTHER PUBLICATIONS

Benjemaa, "A Solution for the Registration of Multiple 3D Point Sets Using Unit Quaternions", ECCV98, 5th European Conference on Computer Vision, Jun. 1998, vol. II, pp. 34-50.

(Continued)

*Primary Examiner* — Allen Wong

(57) ABSTRACT

In a system or method where three-dimensional data is acquired as a sequence of frames of data along a camera path, disparate sequences are related to one another through a number of geometric stitches obtained by direct registration of three-dimensional data between frames in the disparate sequences. These geometric stitches are then used in addition to or in place of other camera path relationships to form a single virtual stitch graph for the combined model, upon which an integrated global path optimization can be performed.

24 Claims, 9 Drawing Sheets

(51) Int. Cl.
- *A61B 1/24* (2006.01)
- *G06T 19/00* (2011.01)
- *G06T 7/00* (2006.01)

(52) U.S. Cl.
CPC ......... *A61B1/00039* (2013.01); *A61B 1/00193* (2013.01); *A61B 1/24* (2013.01); *G06T 7/0024* (2013.01); *G06T 19/00* (2013.01); *G06T 2207/10028* (2013.01); *G06T 2207/20072* (2013.01); *G06T 2207/30036* (2013.01)

(56) References Cited

U.S. PATENT DOCUMENTS

| | | | |
|---|---|---|---|
| 7,372,642 B2 | 5/2008 | Rohaly | |
| 2003/0151604 A1 | 8/2003 | Kaufman | |
| 2004/0155975 A1 | 8/2004 | Hart | |
| 2006/0139470 A1 | 6/2006 | McGowan | |
| 2007/0103460 A1 | 5/2007 | Zhang | |
| 2007/0171220 A1 | 7/2007 | Kriveshko | |
| 2007/0172101 A1 | 7/2007 | Kriveshko | |
| 2010/0066364 A1 | 3/2010 | Huwer | |
| 2010/0194863 A1* | 8/2010 | Lopes | G06T 7/0061 348/50 |
| 2010/0281370 A1 | 11/2010 | Rohaly | |
| 2010/0303341 A1* | 12/2010 | Hausler | A61B 5/0062 382/154 |

OTHER PUBLICATIONS

Dorst, "First Order Error Propagation of the Procrustes Method for 3D Attitude Estimation", IEEE Transactions on Pattern Analysis and Machine Intelligence, Feb. 2005, vol. 27, No. 2, pp. 221-229.

Govindu "Combining Two-View Constraints For Motion Estimation,", Proc. of the Int. Conf. on Computer Vision and Pattern Recognition, Jul. 2001, vol. 2, pp. 218-225.

Krishnan, "Global Registration of Multiple 3D Point Sets via Optimization-on-a-Manifold", Eurographics Symposium on. Geometry Processing, 2005, 11 pages.

Williams, "Simultaneous Registration Of Multiple Corresponding Point Sets", Computer Vision and Image Understanding, Jan. 2001, vol. 81, No. 1, pp. 117-142.

International Search Report for International PCT Application No. PCT/US2012/025554 Mailed on Sep. 26, 2012, 3 pages.

* cited by examiner

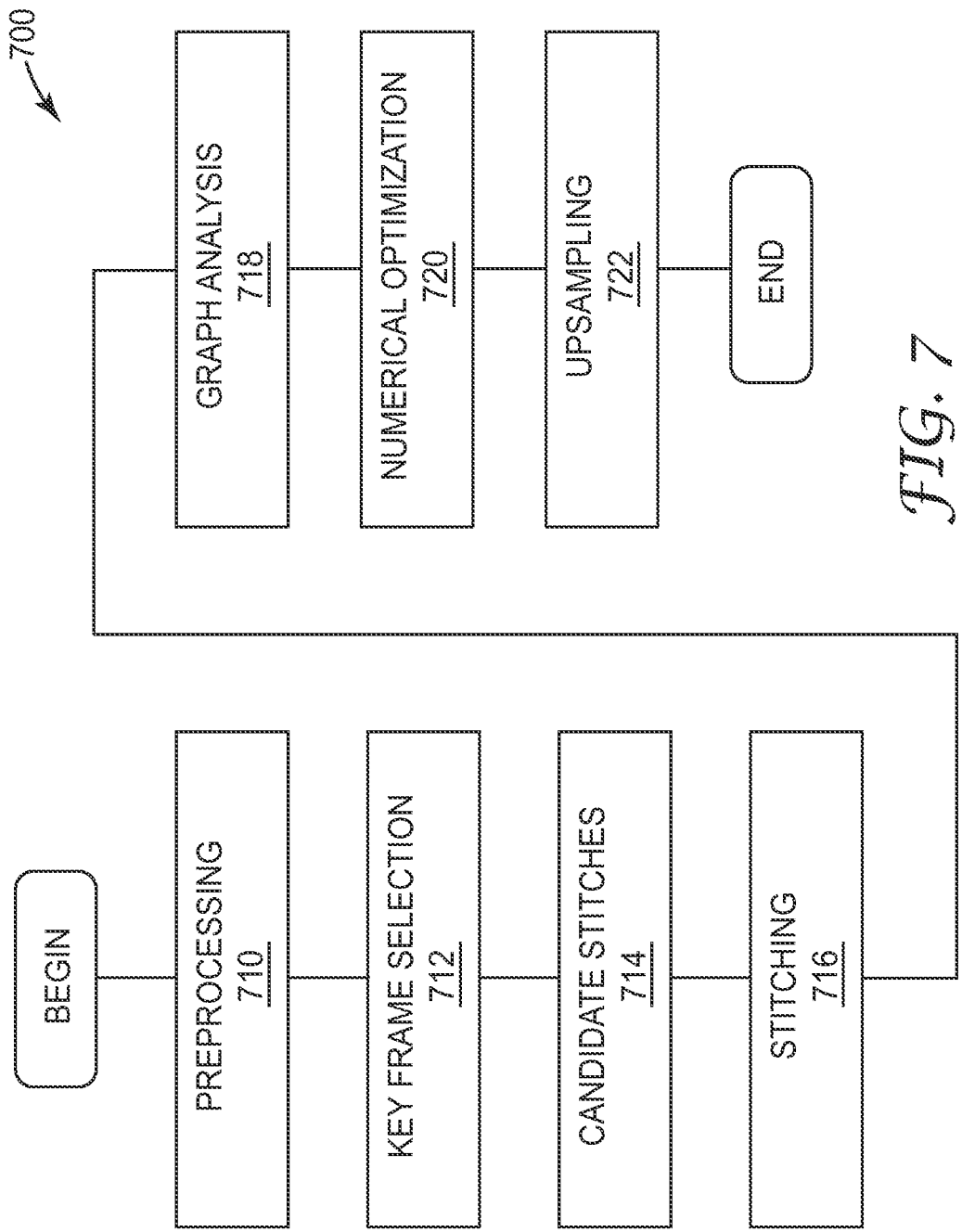

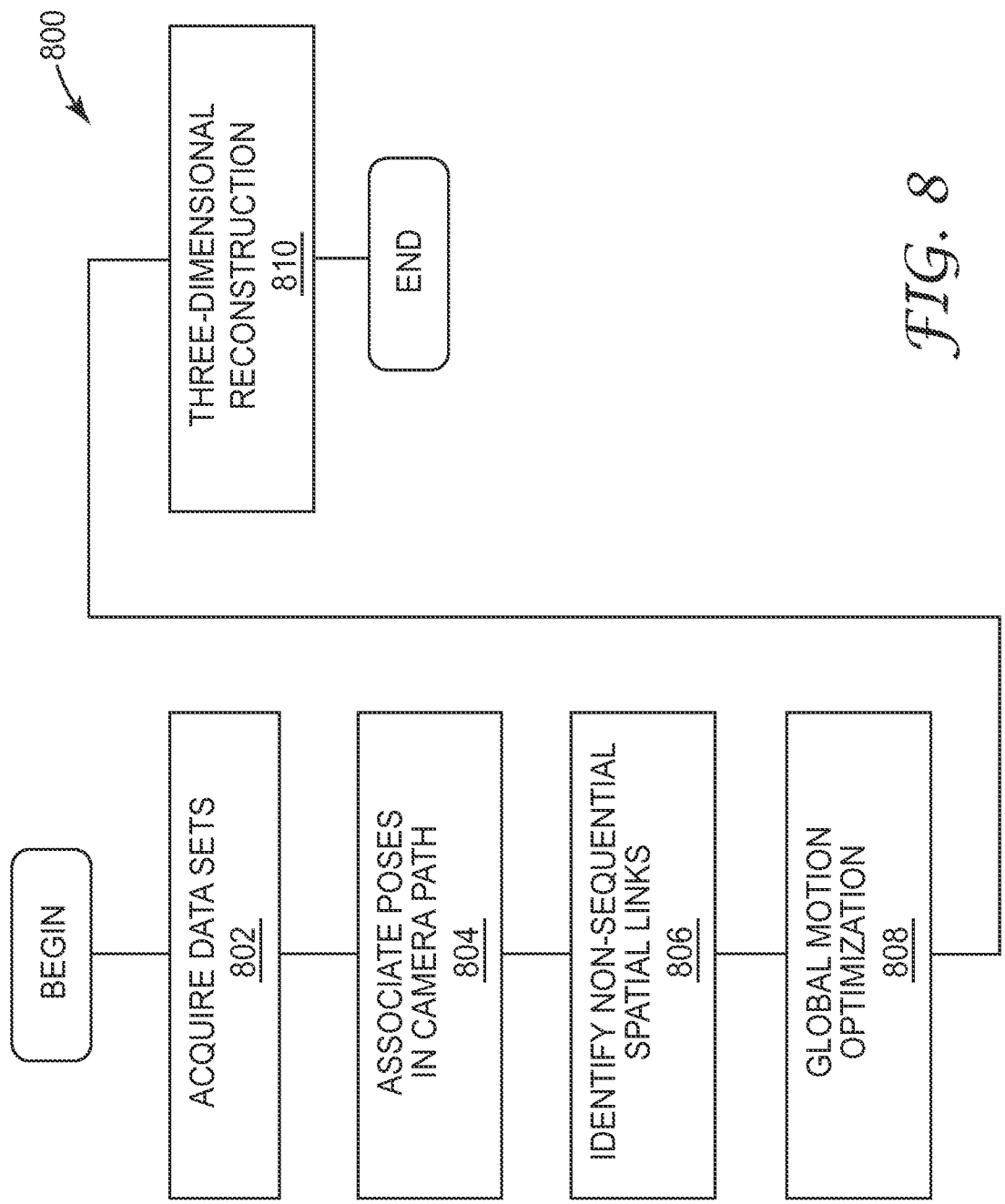

HYBRID STITCHING

FIELD OF INVENTION

This invention relates generally to three-dimensional imaging and more specifically techniques for combining disparate scans of a common three-dimensional surface.

BACKGROUND

In one technique for three-dimensional image reconstruction, a number of images or image sets of an object are captured with a camera that travels in a path over the surface of the object. A three-dimensional model of the object can then be obtained from a description of the camera path and individual three-dimensional measurements captured along the camera path. In certain applications, data from a surface of an object is available in multiple, disparate data sets, such as where a scan is interrupted prior to completion or where additional scans are performed to augment an initial scan. The resulting multiple models can be registered to one another to obtain a combined model. While conventional registration techniques can minimize an error in alignment between two such resulting models, this approach does not afford an opportunity to refine the individual models in view of the combined data.

There remains a need for improved techniques to combine disparate three-dimensional data sets, particularly disparate data sets based upon a path of poses of a three-dimensional scanner.

SUMMARY

In a system or method where three-dimensional data is acquired as a sequence of frames of data along a camera path, disparate sequences are related to one another through a number of geometric stitches obtained by direct registration of three-dimensional data between frames in the disparate sequences. These geometric stitches are then used in addition to or in place of other camera path relationships to form a single virtual stitch graph for the combined model, upon which an integrated global path optimization can be performed.

BRIEF DESCRIPTION OF THE DRAWINGS

The invention and the following detailed description of certain embodiments thereof may be understood by reference to the following figures.

FIGS. 6A and 6B illustrate accumulated error in camera paths.

FIG. 7 is a flow chart of a three-dimensional reconstruction process including global path optimization for improved accuracy.

FIG. 8 is a flow chart of a dental object reconstruction process using numerical optimization.

DETAILED DESCRIPTION

Figure 1:
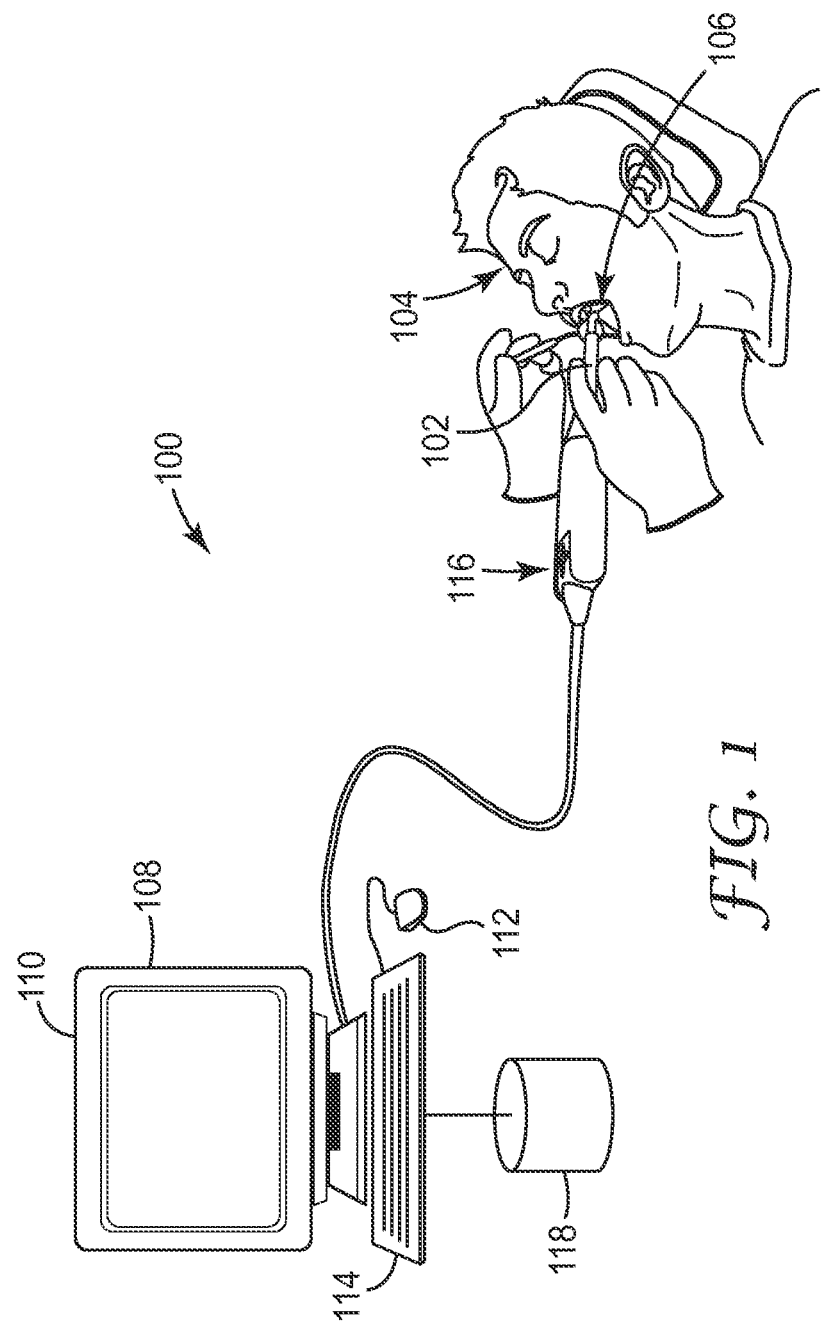
FIG. 1 shows a three-dimensional scanning system.

In the following text, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

In the systems and methods described herein, a number of techniques for global motion optimization are employed to improve accuracy of three-dimensional reconstructions based upon camera path.

The following description details specific scanning technologies and focuses on dental applications of three-dimensional imaging; however, it will be appreciated that variations, adaptations, and combinations of the methods and systems below will be apparent to one of ordinary skill in the art. For example, while an image-based system is described, non-image based scanning techniques such as infrared time-of-flight techniques or structured light techniques using patterned projections may similarly employ reconstruction based on camera path that may benefit from the improvements described herein. As another example, while digital dentistry is one useful application of the improved accuracy that results from the techniques described herein, global path optimization may also usefully be employed to refine three-dimensional animation models or three-dimensional scans for machine vision applications or for mapping applications. All such variations, adaptations, and combinations are intended to fall within the scope of this disclosure.

In the following description, the term "image" generally refers to a two-dimensional set of pixels forming a two-dimensional view of a subject within an image plane. The term "image set" generally refers to a set of related two-dimensional images that might be resolved into three-dimensional data. The term "point cloud" generally refers to a three-dimensional set of points forming a three-dimensional view of the subject reconstructed from a number of two-dimensional images. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional model", "three-dimensional surface representation", "digital surface representation", "three-dimensional surface map", and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that a variety of three-dimensional rendering technologies exist, and may be usefully employed with the systems and methods disclosed herein. For example, the system and methods described herein may usefully employ a holographic display, an autostereoscopic display, an anaglyph display, a head-mounted stereo display, or any other two-dimensional and/or three-dimensional display. As such, rendering as described herein should be interpreted broadly unless a narrower meaning is explicitly provided or otherwise clear from the context.

The term "dental object", as used herein, is intended to refer broadly to subject matter related to dentistry. This may include intraoral structures such as dentition, and more typically human dentition, such as individual teeth, quadrants, full arches, pairs of arches (which may be separate or in occlusion of various types), soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects such as the restorations, prostheses, appliances, hardware, and interim components of dental manufacture as described above.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

It will further be understood that terms such as "tool" or "control", when used to describe aspects of a user interface, are intended to refer generally to a variety of techniques that may be employed within a graphical user interface or other user interface to receive user input that stimulates or controls processing including without limitation drop-down lists, radio buttons, cursor and/or mouse actions (selections by point, selections by area, drag-and-drop operations, and so forth), check boxes, command lines, text input fields, messages and alerts, progress bars, and so forth. A tool or control may also include any physical hardware relating to the user input, such as a mouse, keyboard, display, keypad, track ball, and/or any other device that receives physical input from a user and converts the physical input into an input for use in a computerized system. Thus in the following description the terms "tool", "control" and the like should be broadly construed unless a more specific meaning is otherwise provided or clear from the context.

FIG. 1 depicts a three-dimensional scanning system that may be used with the systems and methods described herein. In general, the system 100 may include a scanner 102 that captures images from a surface 106 of an object 104, such as a dental patient, and forwards the images to a computer 108, which may include a display 110 and one or more user-input devices 112, 114 such as a mouse 112 or a keyboard 114. The scanner 102 may also include an integrated input or output device 116 such as a control input (for example, button, touchpad, thumbwheel, etc.) or a display (for example, LCD or LED display) to provide status information.

The scanner 102 may include any camera or camera system suitable for capturing images from which a three-dimensional point cloud or other three-dimensional data may be recovered. For example, the scanner 102 may employ a multi-aperture system as disclosed in U.S. Pat. No. 7,372,642 to Rolhály et al. While Rolhály discloses one multi-aperture system, it will be appreciated that any multi-aperture system suitable for reconstructing a three-dimensional point cloud from a number of two-dimensional images may similarly be employed. In one multi-aperture embodiment, the scanner 102 may include a plurality of apertures including a center aperture positioned along a center optical axis of a lens that provides a center channel for the scanner 102, along with any associated imaging hardware. In such embodiments, the center channel may provide a conventional video image of the scanned subject matter, while a number of axially offset channels yield image sets containing disparity information that can be employed in three-dimensional reconstruction of a surface. In other embodiments, a separate video camera and/or channel may be provided to achieve the same result, that is, a video of an object corresponding temporally to a three-dimensional scan of the object, preferably from the same perspective, or from a perspective having a fixed, known relationship to the perspective of the scanner 102. The scanner 102 may also, or instead, include a stereoscopic, triscopic or other multi-camera or other configuration in which a number of cameras or optical paths are maintained in fixed relation to one another to obtain two-dimensional images of an object from a number of different perspectives. The scanner 102 may include suitable processing for deriving a three-dimensional point cloud from an image set or a number of image sets, or each two-dimensional image set may be transmitted to an external processor such as contained in the computer 108 described below. In other embodiments, the scanner 102 may employ structured light, laser scanning, direct ranging, or any other technology suitable for acquiring three-dimensional data, or two-dimensional data that can be resolved into three-dimensional data. While the techniques described below can usefully employ video data acquired by a video-based three-dimensional scanning system, it will be understood that any other three-dimensional scanning system may be supplemented with a video acquisition system that captures suitable video data contemporaneously with, or otherwise synchronized with, the acquisition of three-dimensional data.

In one embodiment, the scanner 102 is a handheld, freely-positionable probe having at least one user-input device 116, such as a button, lever, dial, thumb wheel, switch, or the like, for user control of the image capture system 100 such as starting and stopping scans. In an embodiment, the scanner 102 may be shaped and sized for dental scanning. More particularly, the scanner may be shaped and sized for intraoral scanning and data capture, such as by insertion into a mouth of an imaging subject and passing over an intraoral surface 106 at a suitable distance to acquire surface data from teeth, gums, and so forth. The scanner 102 may, through such a continuous data acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthetic, to ensure proper fitting using a previous scan of corresponding dentition, such as a tooth surface prepared for the prosthetic.

Although not shown in FIG. 1, it will be appreciated that a number of supplemental lighting systems may be usefully employed during image capture. For example, environmental illumination may be enhanced with one or more spotlights illuminating the object 104 to speed image acquisition and improve depth of field (or spatial resolution depth). The scanner 102 may also, or instead, include a strobe, flash, or other light source to supplement illumination of the object 104 during image acquisition.

The object 104 may be any object, collection of objects, portion of an object, or other subject matter. More particularly with respect to the dental techniques discussed herein, the object 104 may include human dentition captured intraorally from a dental patient's mouth. A scan may capture a three-dimensional representation of some or all of the dentition according to particular purpose of the scan. Thus the scan may capture a digital model of a tooth, a quadrant of teeth, or a full collection of teeth including two opposing arches, as well as soft tissue or any other relevant intraoral structures. The scan may capture multiple representations, such as a tooth surface before and after preparation for a restoration. As will be noted below, this data may be employed for subsequent modeling such as designing a restoration or determining a margin line for same. During the scan, a center channel of the scanner 102 or a separate video system may capture video of the dentition from the point of view of the scanner 102. In other embodiments where, for example, a completed fabrication is being virtually test fitted to a surface preparation, the scan may include a dental prosthesis such as an inlay, a crown, or any other dental prosthesis, dental hardware, dental appliance, or the like. The object 104 may also, or instead, include a dental model, such as a plaster cast, wax-up, impression, or negative impression of a tooth, teeth, soft tissue, or some combination of these.

The computer 108 may include, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. In one current embodiment, the system can be operated to capture more than five thousand points per image set in real time using the techniques described herein, and store an aggregated point cloud of several million points. Of course, this point cloud may further processed to accommodate subsequent data handling, such as by decimating the point cloud data or generating a corresponding mesh of surface data. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the object 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110. In another aspect, the display may include an autostereoscopic display capable of displaying stereo images.

Communications between the computer 108 and the scanner 102 may use any suitable communications link including, for example, a wired connection or a wireless connection based upon, for example, IEEE 802.11 (also known as wireless Ethernet), BlueTooth, or any other suitable wireless standard using, for example, a radio frequency, infrared, or other wireless communication medium. In medical imaging or other sensitive applications, wireless image transmission from the scanner 102 to the computer 108 may be secured. The computer 108 may generate control signals to the scanner 102 which, in addition to image acquisition commands, may include conventional camera controls such as focus or zoom.

In an example of general operation of a three-dimensional image capture system 100, the scanner 102 may acquire two-dimensional image sets at a video rate while the scanner 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system employs camera motion estimation to avoid the need for independent tracking of the position of the scanner 102. One useful example of such a technique is described in commonly-owned U.S. application Ser. No. 11/270,135, filed on Nov. 9, 2005. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In general, the display 110 may be operatively coupled to, and capable of receiving display signals from, the computer 108. This display may include a CRT or flat panel monitor, a three-dimensional display (such as an anaglyph display), an autostereoscopic three-dimensional display or any other suitable two-dimensional or three-dimensional rendering hardware. In some embodiments, the display may include a touch screen interface using, for example capacitive, resistive, or surface acoustic wave (also referred to as dispersive signal) touch screen technologies, or any other suitable technology for sensing physical interaction with the display 110.

The system 100 may include a computer-usable or computer-readable medium. The computer-usable medium 118 may include one or more memory chips (or other chips, such as a processor, that include memory), optical disks, magnetic disks or other magnetic media, and so forth. The computer-usable medium 118 may in various embodiments include removable memory (such as a USB device, tape drive, external hard drive, and so forth), remote storage (such as network attached storage), volatile or non-volatile computer memory, and so forth. The computer-usable medium 118 may contain computer-readable instructions for execution by the computer 108 to perform the processes described herein such as the process described in detail with reference to FIG. 3. The computer-usable medium 118 may also, or instead, store data received from the scanner 102, store a three-dimensional model of the object 104, store computer code for rendering and display, and so forth.

Figure 2:
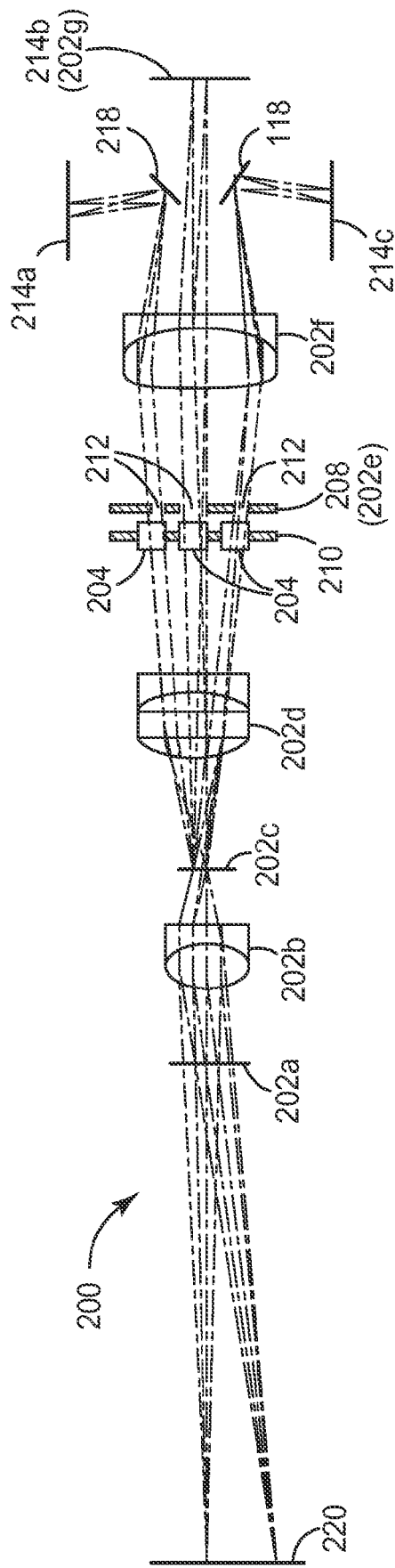
FIG. 2 shows a schematic diagram of an optical system for a three-dimensional scanner.

FIG. 2 depicts an optical system 200 for a three-dimensional scanner that may be used with the systems and methods described herein, such as for the scanner 102 described above with reference to FIG. 1.

The optical system 200 may include a primary optical facility 202, which may be employed in any kind of image processing system. In general, a primary optical facility refers herein to an optical system having one optical channel. Typically, this optical channel shares at least one lens, and has a shared image plane within the optical system, although in the following description, variations to this may be explicitly described or otherwise clear from the context. The optical system 200 may include a single primary lens, a group of lenses, an object lens, mirror systems (including traditional mirrors, digital mirror systems, digital light processors, or the like), confocal mirrors, and any other optical facilities suitable for use with the systems described herein. The optical system 200 may be used, for example in a stereoscopic or other multiple image camera system. Other optical facilities may include holographic optical elements or the like. In various configurations, the primary optical facility 202 may include one or more lenses, such as an object lens (or group of lenses) 202b, a field lens 202d, a relay lens 202f, and so forth. The object lens 202b may be located at or near an entrance pupil 202a of the optical system 200. The field lens 202d may be located at or near a first image plane 202c of the optical system 200. The relay lens 202f may relay bundles of light rays within the optical system 200. The optical system 200 may further include components such as aperture elements 208 with one or more apertures 212, a refocusing facility 210 with one or more refocusing elements 204, one or more sampling facilities 218, and/or a number of sensors 214a, 214b, 214c.

The optical system 200 may be designed for active wavefront sampling, which should be understood to encompass any technique used to sample a series or collection of optical data from an object 220 or objects, including optical data used to help detect two- or three-dimensional characteristics of the object 220, using optical data to detect motion, using optical data for velocimetry or object tracking, or the like. Further details of an optical system that may be employed as the optical system 200 of FIG. 2 are provided in U.S. Pat. No. 7,372,642. More generally, it will be understood that, while FIG. 2 depicts one embodiment of an optical system 200, numerous variations are possible. On salient feature of the optical system related to the discussion below is the use of a center optical channel that captures conventional video or still images at one of the sensors 214b concurrent with various offset data (at, for example, 214a and 214c) used to capture three-dimensional measurements. This center channel image may be presented in a user interface to permit inspection, marking, and other manipulation by a user during a user session as describe below.

Figure 3:
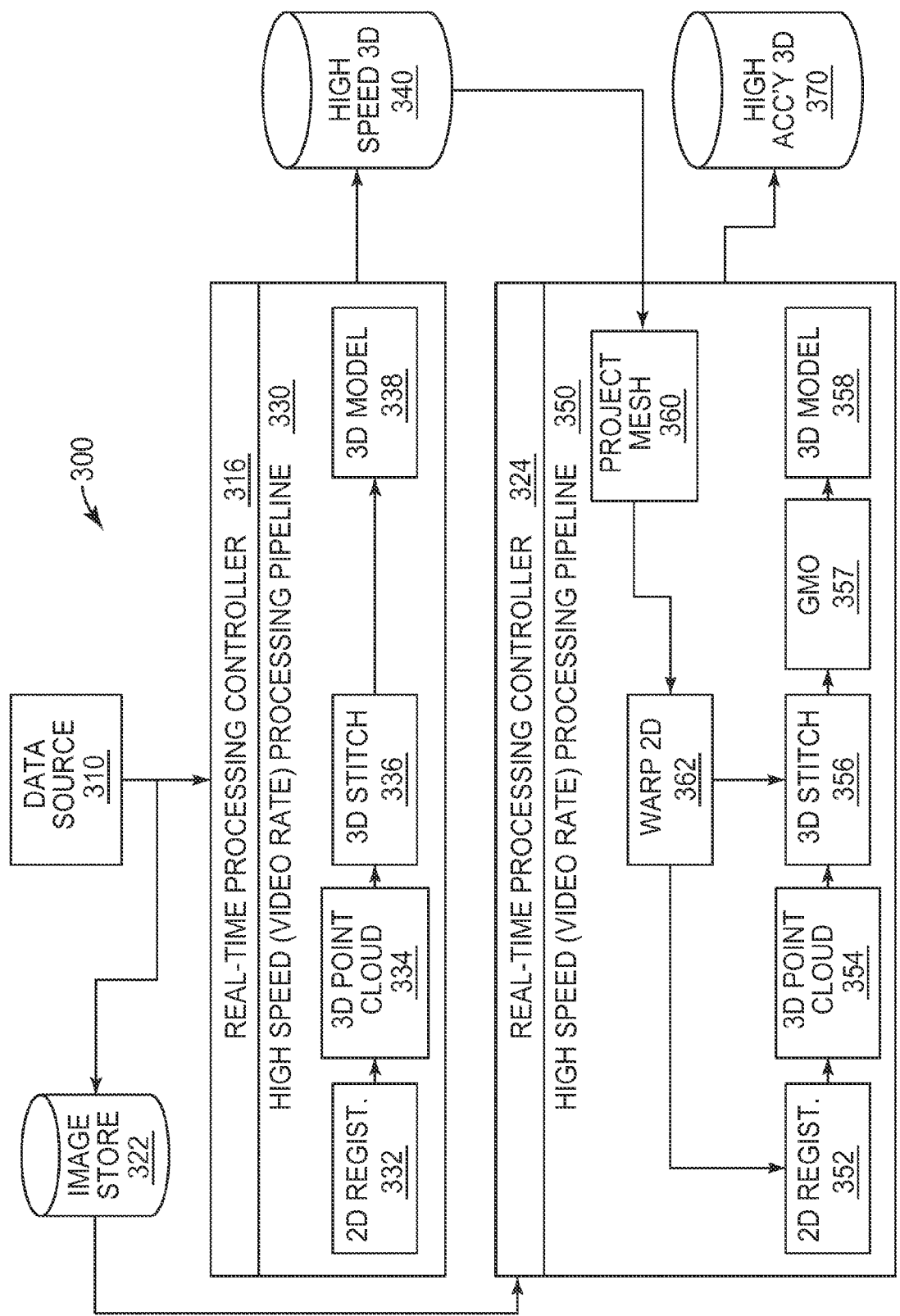
FIG. 3 shows a processing pipeline for obtaining three-dimensional data from a video scanner.

FIG. 3 shows a three-dimensional reconstruction system 300 employing a high-speed pipeline and a high-accuracy pipeline. In general, the high-speed processing pipeline 330 aims to provide three-dimensional data in real time, such as at a video frame rate used by an associated display, while the high-accuracy processing pipeline 350 aims to provide the highest accuracy possible from scanner measurements, subject to any external computation or time constraints imposed by system hardware or an intended use of the results. A data source 310 such as the scanner 102 described above provides image data or the like to the system 300. The data source 310 may for example include hardware such as LED ring lights, wand sensors, a frame grabber, a computer, an operating system and any other suitable hardware and/or software for obtaining data used in a three-dimensional reconstruction. Images from the data source 310, such as center channel images containing conventional video images and side channels containing disparity data used to recover depth information may be passed to the real-time processing controller 316. The real-time processing controller 316 may also provide camera control information or other feedback to the data source 310 to be used in subsequent data acquisition or for specifying data already obtained in the data source 310 that is needed by the real-time processing controller 316. Full resolution images and related image data may be retained in a full resolution image store 322. The stored images may, for example, be provided to the high-accuracy processing controller 324 during processing, or be retained for image review by a human user during subsequent processing steps.

The real-time processing controller 316 may provide images or frames to the high-speed (video rate) processing pipeline 330 for reconstruction of three-dimensional surfaces from the two-dimensional source data in real time. In an exemplary embodiment, two-dimensional images from an image set such as side channel images, may be registered by a two-dimensional image registration module 332. Based on the results of the two-dimensional image registration, a three-dimensional point cloud generation module 334 may create a three-dimensional point cloud or other three-dimensional representation. The three-dimensional point clouds from individual image sets may be combined by a three-dimensional stitching module 336. Finally, the stitched measurements may be combined into an integrated three-dimensional model by a three-dimensional model creation module 338. The resulting model may be stored as a high-speed three-dimensional model 340.

The high-accuracy processing controller 324 may provide images or frames to the high-accuracy processing pipeline 350. Separate image sets may have two-dimensional image registration performed by a two-dimensional image registration module 352. Based on the results of the two-dimensional image registration a three-dimensional point cloud or other three-dimensional representation may be generated by a three-dimensional point cloud generation module 354. The three-dimensional point clouds from individual image sets may be connected using a three-dimensional stitching module 356. Global motion optimization, also referred to herein as global path optimization or global camera path optimization, may be performed by a global motion optimization module 357 in order to reduce errors in the resulting three-dimensional model 358. In general, the path of the camera as it obtains the image frames may be calculated as a part of the three-dimensional reconstruction process. In a post-processing refinement procedure, the calculation of camera path may be optimized—that is, the accumulation of errors along the length of the camera path may be minimized by supplemental frame-to-frame motion estimation with some or all of the global path information. Based on global information such as individual frames of data in the image store 322, the high-speed three-dimensional model 340, and intermediate results in the high-accuracy processing pipeline 350, the high-accuracy model 370 may be processed to reduce errors in the camera path and resulting artifacts in the reconstructed model. As a further refinement, a mesh may be projected onto the high-speed model by a mesh projection module 360. The resulting images may be warped or deformed by a warping module 362. Warped images may be utilized to ease alignment and stitching between images, such as by reducing the initial error in a motion estimation. The warped images may be provided to the two-dimensional image registration module 352. The feedback of the high-accuracy three-dimensional model 370 into the pipeline may be repeated until some metric is obtained, such as a stitching accuracy or a minimum error threshold.

Various aspects of the system 300 of FIG. 3 are described in greater detail below. It should be understood that various processing modules, or the steps implied by the modules, shown in this figure are exemplary in nature and that the order of processing, or the steps of the processing sequence, may be modified, omitted, repeated, re-ordered, or supplemented, without departing from the scope of this disclosure.

Figure 4A:
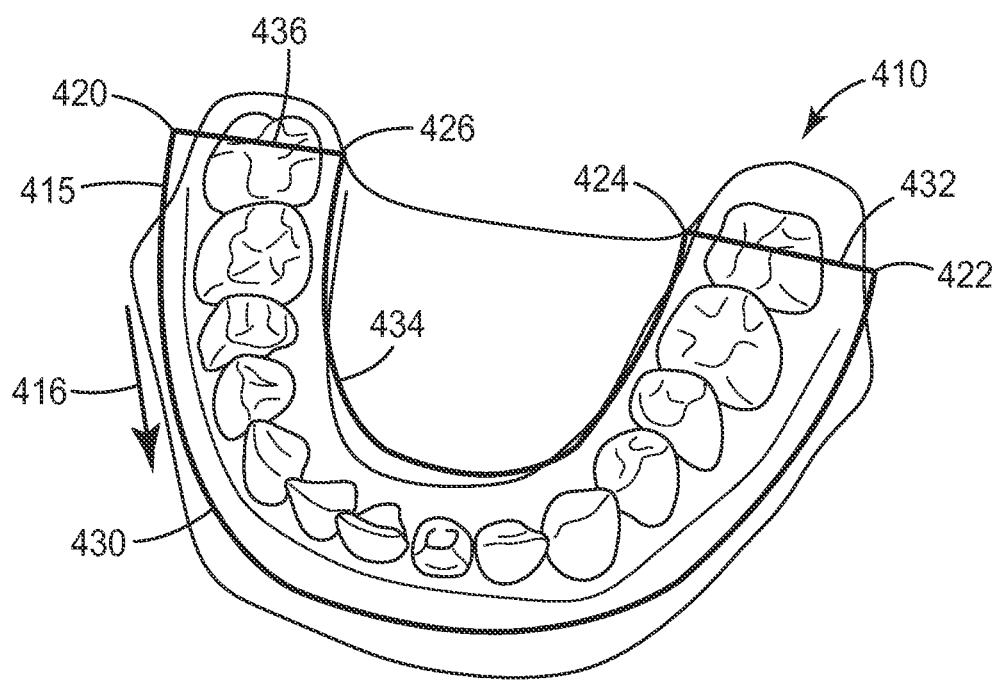
FIGS. 4A and 4B illustrate camera paths for a three-dimensional scanner.

FIG. 4A shows an object 410 for imaging, along with a path 415 that a camera may follow while obtaining a three-dimensional scan of a surface of the object 410. The direction of the path 415 is indicated generally by an arrow 416. The object 410 may be an upper dental impression (as shown) or any other object from which three-dimensional surface data is sought. Starting the camera at a starting point 420, the camera may follow an arc 430 to a second point 422. The camera may then follow a segment 432 to a third point 424. The camera may then follow a second arc 434 to a fourth point 426. The camera may then follow a second segment 436 to return approximately to the starting point 420. It should be noted that the path 415 followed by the camera may be irregular rather than smooth, and that while a particular path 415 is depicted, more generally any path may be taken by the camera including paths that double back upon themselves, cross over identical regions two or more times, and/or entirely skip various surfaces of the object 410. It should also be noted that the camera path 415 may usefully return to the starting point 420, but this is not strictly required for three-dimensional reconstruction as described herein. The camera may take hundreds or thousands of images or more as the camera traverses the path around such a dental object 410.

Figure 4B:
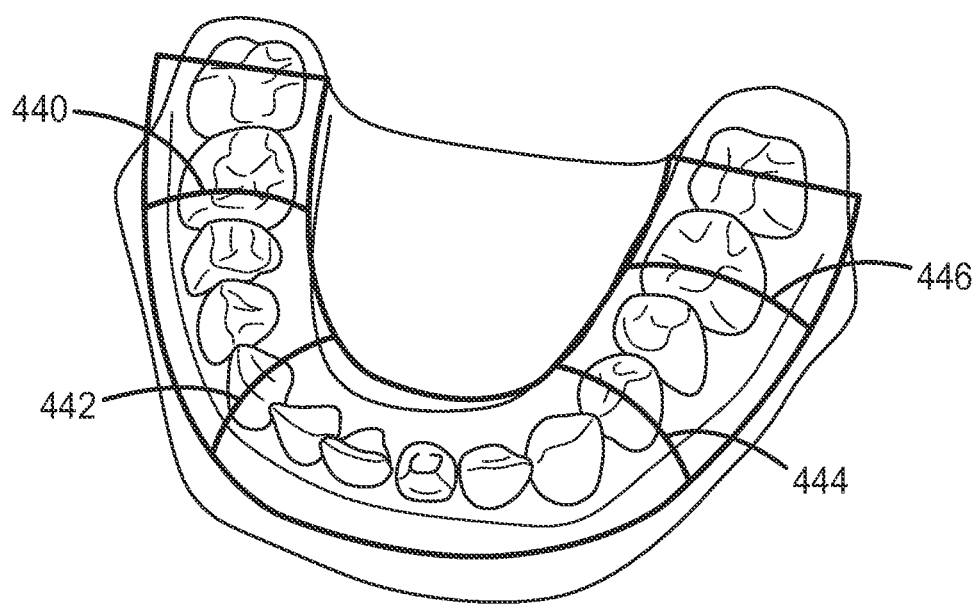

FIG. 4B shows locations where additional scan data might usefully be acquired to improve the accuracy of a three-dimensional reconstruction. For example, arcs 440, 442, 444, and 446 may be scanned (for example, traversed by the camera path) to provide cross linking between various lengths of the camera path. Data might usefully be acquired, for example, from any area that can improve computational accuracy of a three-dimensional reconstruction such as regions where the length of a camera path between two measurements of the surface (for example, image sets or image data) is significantly greater than the distance between the two corresponding surface locations in the world coordinate system for the camera path. It will be appreciated that this may be a Euclidean distance or any suitable proxy for distance. For example, the length of the camera path may be measured in terms of the number of camera path segments, or the number of camera path segments from key frame to key frame, between two camera poses in Euclidean space. As another example, this may include regions where separate three-dimensional measurements for a general region of the reconstructed three-dimensional model fail to register to one another, or other indicia of accumulated error in the global camera path might be present.

Figure 5:
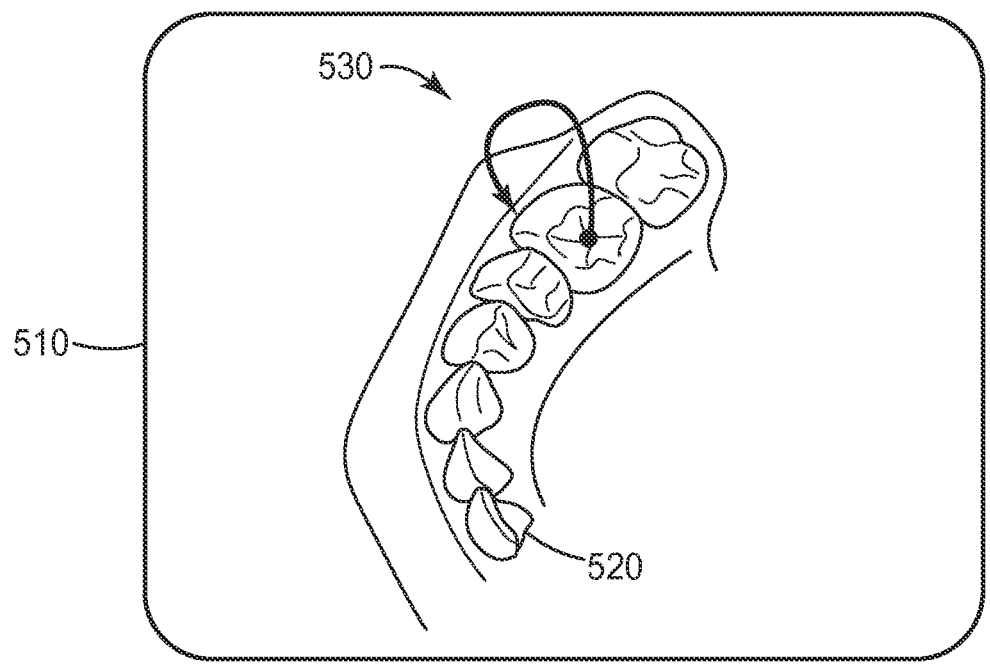
FIG. 5 shows a user interface image where additional data is requested by a software tool.

FIG. 5 shows a user interface depicting a graphical request for additional scan data. After the camera follows the path 415 illustrated above, a software tool may be utilized to identify various locations where additional data might usefully be acquired to reduce accumulated error in a global camera path, such as two frames of image data that represent a candidate for an accumulated error in camera path relative to one another using, for example, any of the techniques described above. A monitor 510 may display an image 520 such as a three-dimensional reconstruction of scanned subject matter, and an arrow 530 may be displayed on the monitor 510 indicating where additional scanning is recommended. The user may then proceed to use a scanner, such as the scanner 102 from FIG. 1, to scan the area indicated by the arrow 530. More generally, areas for additional scanning may be identified to a user in a graphical user interface that displays a reconstructed three-dimensional model from the camera path, along with arrows or other identifiers or graphical annotations that illustrate a recommended scan path. After a user augments a camera path with additional scans, the resulting data can be employed to resolve differences (that is, errors) in the global camera path, as described generally throughout this disclosure.

Figure 6A:
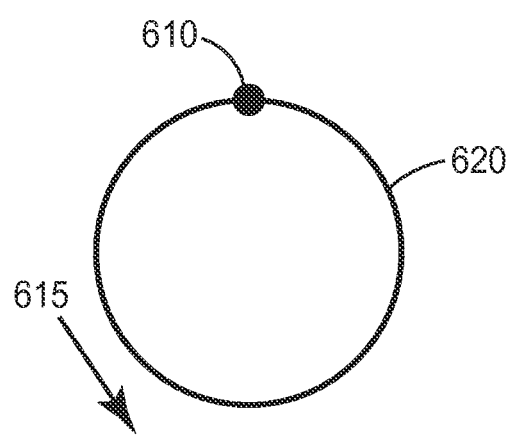
Figure 6A:
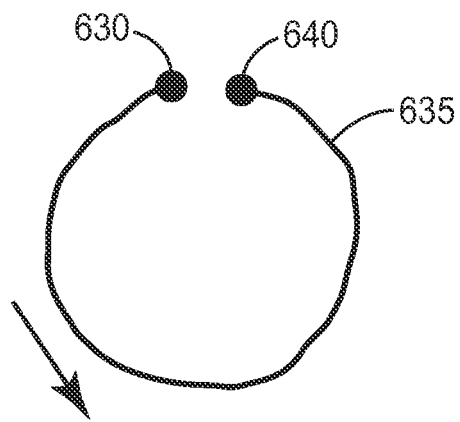

FIG. 6A illustrates a simple camera path in a world coordinate system. The camera starts at a starting point 610 and follows a path 620 in a counterclockwise direction as indicated by an arrow 625, returning to an ending point coincident with the starting point 610 in a fixed coordinate system, such as an arbitrarily selected world coordinate system.

FIG. 6B shows a simple camera path in a camera coordinate system. When a camera traverses the path 620 in the world coordinate system, errors may accumulate in a calculated camera path 635 so that a measured ending point 640 appears to be located away from the measured starting point 630 in the camera coordinate system, even though these points are identical in the world coordinate system. In one aspect, one or more cross links such as those described above with reference to FIG. 4 may be employed to mitigate accumulated errors in the calculated camera path 635.

FIG. 7 is a flow chart of a three-dimensional reconstruction process including global path optimization for improved accuracy.

The process 700 may begin with preprocessing as shown in step 710. It will be understood that preprocessing as described herein presupposes the availability of a number of frames of image data from which a camera path and three-dimensional model can be reconstructed. The information for the three-dimensional reconstruction may be generated in numerous ways including coming from structured light projection, shading based three-dimensional reconstruction, or disparity data. Disparity data may be generated by a conventional image plus one or more other channels or side channels. The preprocessing may include determining the number of available frames, the time duration over which all the frames were taken, the amount of overlap between neighboring frames, identification and elimination of frames with blurred or badly distorted images, and any other suitable preprocessing steps. An estimate of the number of desired key frames may be initially determined during the preprocessing step.

As shown in step 712, key frames may be selected from among all of the frames of data acquired from a scanner along a camera path. In general, computational costs can be reduced by storing certain data and performing certain calculations and processing steps exclusively with reference to key frames. In principle, these key frames should be related to one another in a manner that permits characterization of a camera path, typically through the registration of overlapping three-dimensional data in respective key frames. Various methods are known in the art for selecting a subset of frames of data as key frames, including techniques based on image overlap, camera path distance, the number of intervening non-key frames and so forth. For example, key frames may be selected based on time duration from an immediately preceding key frame. Key frames may also or instead be selected based upon an amount of image overlap from the preceding key frame and/or a candidate for a following key frame (if available). Too little overlap makes frame-to-frame registration difficult. Too much overlap drives larger numbers of key frames and therefore larger amounts of data to analyze. Key frames may be selected based on spatial displacement, meaning that an upper limit may be placed on the amount of overlap from one key frame to the next. Key frames may also be selected based on sequential displacement. This type of sequential displacement could mean that every tenth frame is determined to be a key frame, for example. In one aspect, key frames may be selected as data is acquired based on any number of suitable criteria. In another aspect, key frame pairs may be determined post hoc by examining all possible candidate key frames. All possible key frame pairs may be examined and candidates may be removed, for example, where there is insufficient overlap to form a stitch. Still more generally, any technique suitable for selecting a subset of frames in a data set may be usefully employed to select key frames for processing in order to reduce computational complexity.

Once key frames have been selected, additional processing may be performed. For example, full image data (for example, full resolution center and side channel images) may be stored for each key frame, along with image signature data, point cloud centroid calculations, and any other measured or calculated data to support use of the key frames in a three-dimensional reconstruction process as described herein.

As shown in step 714, candidate stitches may be identified. In general, a stitch is a relationship between two separate three-dimensional measurements from two different camera positions. Once a stitch is established, a rotation and a translation may be determined for the path of a camera between the two different camera positions. In a complementary fashion, the three-dimensional measurements from the two different camera positions may be combined into a portion of a three-dimensional model. Candidate stitches may be analyzed around each key frame, such as from the key frame to some or all of the frames of data between the key frame and neighboring key frames. Stitches may be based on the originally imaged frames. It may also be useful to deform or warp two-dimensional images during registration and other steps in a stitching process in order to improve accuracy and/or speed each stitch calculation. Stitches may also or instead be based on other observed epipolar relationships in source data.

As shown in step 716, stitches may be selected for the complete camera path from the universe of candidate stitches. The selection of stitches may be made based upon, for example, the lowest calculated error in resulting portions of the three-dimensional model.

As shown in step 718, a graph analysis may be performed using the key frames and the associated stitching to calculate a global path for the camera used to obtain a three-dimensional model. The graph analysis may consider each key frame as a node or vertex and each stitch as an edge between a pair of nodes. A key frame is selected as a starting point. A breadth- or depth-first search may be performed through the graph to identify stitches which may connect the current key frame to another key frame. Each key frame is marked as the graph is proceeded through. A check may be performed to see if all key frames have been reached within the graph. If all key frames have not been reached through traversing stitches in the graph analysis, the largest sub-graph is identified. This sub-graph may be examined to see if the entire three-dimensional image may be modeled.

It may be that certain sub-graphs are not required to complete the three-dimensional imaging. If the camera lingered over a particular region of a surface of an object, or if the camera looped on a region multiple times, the associated sub-graph(s) may not be needed. If a separate sub-graph is identified, which is needed to complete the three-dimensional imaging, an optional branch back to step 712 may be performed. For example, a set of key frames may have been selected which did not have sufficient stitching from one key frame to the next key frame. By choosing a different set of key frames, sufficient stitching may be obtained in order to obtain a complete graph of all needed aspects of the three-dimensional imaging. A key frame which is too sparse, meaning it has insufficient stitches to aid in building a graph, may indicate that a different set of key frames should be selected. Based on the graph analysis, a global path may be selected, and the graph may then be analyzed to optimize the path calculation.

As shown in step 720, a numerical optimization may be performed to reduce errors in the calculated camera path based upon available data for the complete camera path such as, for example, cross links that interrelate temporally distant measurements. In general, the objective of numerical optimization is to minimize a calculated error based upon an error function for the camera path and/or reconstructed three-dimensional model. A useful formulation of the error minimization problem for a global camera path is presented below.

There may be a set of candidate camera positions and orientations referenced to a world coordinate system. A camera position and orientation collectively may be referred to as a camera pose. There may be a set of measured frame-to-frame camera motions. A camera translation and rotation collectively may be referred to as a camera motion. A measured camera motion may be referenced in the coordinate system of one camera pose. An example set of three key frames may be obtained from three camera positions, A, B, and C, each of which may be referenced to an origin, O, of a world coordinate system in three-dimensional space. In addition to the position of these points, a camera at each of these points may have a different orientation. A combination of the position and orientation is generally referred to as a camera pose. Between each of these points are motion parameters including a translation (a change in position) and a rotation (a change in orientation). The relationship between a point, X, expressed in the world coordinate system as $X_O$ and the same point expressed in the A coordinate system, $X_A$ may be given by equation (1):

$$X_A = R_{OA} X_O + T_{OA} \qquad (1)$$

$R_{OA}$ is the rotation, taking points from the world to the A coordinate system. $T_{OA}$ is the translation of the world coordinate system as represented in the A coordinate system. It should be understood that symbols X and T may represent a vector, rather than a scalar, for example where X includes x, y, and z coordinate values. Further, it should be understood that symbol R may represent a matrix. Equations (2) and (3) may similarly represent a transform transformation between the world and the B and C coordinate systems respectively:

$$X_B = R_{OB} X_O + T_{OB} \qquad (2)$$

$$X_C = R_{OC} X_O + T_{OC} \qquad (3)$$

By rearranging, equation (1) and equation (2) may be represented as shown in equation (4):

$$X_O = R_{OA}^{-1}(X_A - T_{OA}) = R_{OB}^{-1}(X_B - T_{OB}) \quad (4)$$

The representation of a point in one camera's coordinate system may be related to the same point in another coordinate system. For example, as in equations 1-3, coordinates of a point, X, may be transformed from the A coordinate system to the B coordinate system as follows:

$$X_B = R_{AB} X_A + T_{AB} \quad (5)$$

The rotation $R_{AB}$ rotates points from the A to the B coordinate system and $T_{AB}$ is the position translation of the origin of the A coordinate system in the B coordinate system.

In an optimization, the pose of every camera may be optimized based on measured transforms between camera poses. That is, a number of camera-to-world or world-to-camera rotations and translations, for example, $R_{On}$ and $T_{On}$ may be performed. It will be appreciated that the world coordinate system is arbitrary, and one of these transforms may conveniently be an identity rotation with zero translation, or a constant motion transfer can be applied to all camera poses without altering the underlying optimization.

The rotations and translations may be measured for many pairs of cameras. For the ith such measured frame-to-frame motion, let one of the cameras of the pair be camera A and the other be camera B. This may also be considered the ith stitch that relates the camera poses for A and B. Let $R_{AB}^i$ be the measured rotation taking points in the A system to the B system and $T_{AB}^i$ be the coordinates of the A position expressed in the B system, as in equation (5).

The rotations and translations for all cameras, $R_{On}$ and $T_{On}$ may be optimized. It will be appreciated that, while these expressions and the following discussion are cast in terms of rotations and translations from the individual camera coordinate systems to a single world coordinate system, this characterization is not intended to limit the generality of this disclosure. A similar or complementary analysis may be performed using the reverse of these transforms, or any other transform or collection of transforms (typically, although not necessarily rigid transforms) capable of describing a camera path across multiple poses. The constraints on camera motion from one pose, A, to another pose, B, for an $i^{th}$ stitch or relationship may be expressed relative to a world coordinate system as rotations, $R_{C,OA}^i$ and $R_{C,OB}^i$, and translations, $T_{C,OA}^i$ and $T_{C,OB}^i$. This relationship is further constrained by the camera path from A to B, which may be expressed as a rotation and a translation as follows:

$$R_{C,AB}^i = R_{C,OB}^i (R_{C,OA}^i)^{-1} \quad (6)$$

$$T_{C,AB}^i = T_{C,OB}^i - R_{C,AB}^i T_{C,OA}^i \quad (7)$$

Note that with sufficient stitches, these relationships may form an overdetermined system of motion constraint equations. Using these equations as a starting point, numerical optimization may be performed on the rotational and translational components of each camera pose based on the measured stitches.

In a decoupled optimization, the rotational and translational components may be independently optimized. This approach may generally be used where there are constraints on one component (for example, rotation) that do not depend on the other component. Given a candidate set of camera rotations, $R_C^i$, the corresponding candidate camera-to-camera rotations, $R_{C,AB}^i$, may be computed that correspond to each of the measured camera-to-camera rotations, $R_{AB}^i$. The corresponding residual rotations, which should be identity in an error free camera path, are given by $R_{residual,AB}^i = R_{C,AB}^i (R_{AB}^i)^{-1}$. A scalar-valued rotational cost function, $e_r$, may be computed that depends on the candidate camera rotations:

$$e_r(R_{C,On}) = \sum_{i=1}^{\#stitches} r_r^{iT} r_r^i, \quad \text{where } r_r^i = \log_{SO(3)} R_{residual,AB}^i \quad (8)$$

In equation (8), $\log_{SO(3)}(R)$ returns an axis-angle vector, $v$, that corresponds to the rotation R. In other words, $\log_{SO(3)}(R)$ returns the vector, $v$, that has a cross-product matrix, $[v]_x$, that is the matrix logarithm of R.

Next, a similar scalar-valued cost function may be computed for translation that depends on the candidate rotations and translations.

$$e_t(R_{C,On}, T_{C,On}) = \sum_{i=1}^{\#stitches} r_t^{iT} r_t^i, \quad \text{where } r_t^i = T_{C,AB}^i - T_{AB}^i \quad (9)$$

In one conventional, decoupled approach to solving these simultaneous systems of equations, the rotational error function may be converted into a quaternion expression in order to translate the numerical problem into a linear system of equations for solution, as described for example in *Combining two-view constraints for motion estimation*, Govindu V., Proc. of the Int. Conf. on Computer Vision and Pattern Recognition, vol. 2, pp. 218-225 (July 2001). While this approach may be numerically convenient, it does not enforce the unit norm constraint for the quaternion solution, which may result in inaccuracy. Thus in one aspect, a path optimization technique may be improved by minimizing equation (8) for rotation as a nonlinear optimization and minimizing equation (9) for translation as a linear optimization. In another aspect, the more computationally efficient linear system of equations may be used to generate an initial estimate for an iterative optimization that uses non-linear optimization.

More generally, the decoupled approach described above may fail to provided a truly optimal result, in a maximum-likelihood sense, where it cannot use information from the translation portion of the stitches in determining rotation. Nonetheless, a substantial amount of work in this field aims to overcome the disadvantages of decoupled optimization, as described for example in *A solution for the registration of multiple 3D point sets using unit quaternions*, Benjemaa R. and F. Shmitt, Proc. ECCV '98, pp. 34-50 (June 1998); *Global registration of multiple 3D point sets via optimization-on-a-manifold*, Krishnan S., Lee P. Y., Moore J. B., Venkatasubramanian S., Eurographics Symp. Geometry Processing (2005); and *Simultaneous registration of multiple corresponding point sets*, Williams J., Bennamoun M., Computer Vision and Image Understanding, vol. 81, no. 1, pp. 117-142 (2001).

In one aspect disclosed herein, a coupled approach to optimization may instead be used to minimize overall error in a camera path. In order to achieve a coupled optimization a weighting may be used to balance the contributions of rotational and translational components to a combined cost function:

$$e_c(R_{C,On}, T_{C,On}) = \sum_{i=1}^{\#stitches} \left( \begin{bmatrix} r_t^i \\ r_r^i \end{bmatrix}^T W_c^i \begin{bmatrix} r_t^i \\ r_r^i \end{bmatrix} \right) \quad (10)$$

Multiple approaches may be used to weight the relative contribution of translations and rotations. In one embodiment the weights may be expressed as matrices, with different stitches receiving different weightings based upon any of a number of factors. For example, the weights may be based on the number of points in a stitch (for example, the shared content), the quality of a particular three-dimensional measurement, and/or any other factors impacting the known reliability of a stitch. In one approach, the weight matrices may also account for anisotropic error in the individual points collected, such as due to acquisition of depth information from disparity measurements, which results in measurement precision that varies with distance from the camera.

In some cases, equation (10) may be reformulated so that the rotation and translation weights are decoupled for each stitch (that is, $W_c^i$ is a block diagonal). In particular, this may occur in the case that the motion stitches are recovered from three-dimensional point correspondences with isotropic point error. In that case, for a given stitch i, between poses A and B, the optimal solution may bring the point cloud as seen from pose A into correspondence with that seen from pose B. If $\overline{X}_A^i$ and $\overline{X}_B^i$ are the positions of the center of the point cloud in the A and B systems respectively, then if $r_t^i$ is replaced in equation (10) with the residual displacement between the point-cloud centers based on the candidate camera pose. This latter residual displacement may be expressed as:

$$r_{t,ctr}^i = \overline{X}_B^i - (R_{C,AB}\overline{X}_A^i + T_{C,AB}^i) \quad (11)$$

Equation (10) may then be reformulated as:

$$e_c(R_{C,On}, T_{C,On}) = \sum_{i=1}^{\#stitches} \left( r_{t,ctr}^{iT} W_r^i r_{t,ctr}^i + r_r^{iT} W_r^i r_r^i \right) \quad (12)$$

In general, by minimizing equation (10), both rotational errors and translational errors may be minimized simultaneously. The weight matrices can be chosen for example according to "First Order Error Propagation of the Procrustes Method for 3D Attitude Estimation" by Leo Dorst, IEEE Transactions on Pattern Analysis and Machine Intelligence, Vol. 27, No. 2, pp. 221-9 (February 2005). Once a more consistent set of motion parameters has been generated the three-dimensional model may be updated.

When total error or some portion of error has been minimized, the resulting value may be evaluated. The calibration state of the scanner and associated equipment may be evaluated based on the minimized error values. If a minimized error falls beyond a certain threshold then calibration for the scanner and associated hardware may be recommended. The threshold value may be empirically determined based on the specific scanner hardware equipment or it may be learned experientially over time for a given system. When a system is new or has been freshly aligned, expected minimized error values may be obtained. When minimized error values deviate from these expected values, a calibration state evaluation flag may be set indicating that the tool should be calibrated. Thus in one aspect, a coupled (or uncoupled) error function may be employed to validate calibration and determine when re-calibration of a device is appropriate.

As shown in step 722, upsampling may be performed to augment a three-dimensional model with data from non-key frames. In general, upsampling may include any technique for addition of data to a result. For example, while the global optimization described above generally refers to optimization among key frames in a contiguous camera path, the resulting optimized three-dimensional model may be supplemented by registering non-key frames to one or more nearby key frames in a manner that creates small, local reconstruction patches that include additional three-dimensional detail available from non-key frames. Or upsampling may be performed by correcting the corresponding camera path for non-key frames according to a globally optimized path for the key frames. Thus in one aspect, upsampling may more generally be understood as any use of optimized data to incorporate related, non-optimized data into a camera path or three-dimensional model.

FIG. 8 shows a reconstruction process 800 using numerical optimization as described above. In one aspect, this optimization technique may be usefully applied to minimize errors in a camera path where spatial links between non-sequential camera poses (or corresponding data sets used to recover three-dimensional surface data) can be identified. For example, where a scan path covers a buccal surface followed by an occlusal or lingual surface, many spatial links might be identified between non-contiguous camera path segments associated with each surface. Under these conditions, a global optimization may significantly improve the accuracy of a three-dimensional reconstruction by reducing errors in the motion estimation parameters for the camera path. It will be understood that the disclosed method may also or instead be embodied in a computer program, a computer program product, or an apparatus embodying any of the foregoing.

As shown in step 802, the process may begin with acquiring data sets such as a data set from a surface of a dental object with a hand-held scanner from each one of a sequence of poses along a camera path, thereby providing a plurality of data sets. The hand-held scanner may, for example, be the video-based scanner described above. The hand-held scanner may instead include any other type of hand-held scanner suitable for intraoral dental scanning, such as a time-of-flight scanner, a structured light scanner, and so forth. The data sets may be any corresponding data acquired for each camera pose that is used to recover three-dimensional data.

It should be understood that in this context, the camera path may correspond to a physical camera path that describes the path actually taken by a scanner during a scan, or the camera path may also or instead include a virtual camera path formed from a plurality of different physical camera paths or other virtual camera paths that intersect with one another. Such a virtual camera path may be created wherever poses from two or more physical paths can be interrelated in a global coordinate system, as established for example by three-dimensionally registering two different scans of the same physical subject matter. The use of virtual camera paths may be particularly useful, for example, where a large scan such as a full arch scan is created from data acquired during two or more discontinuous scanning sessions. Under these conditions, global optimization of a virtual camera path can be used to improve consistency of the combined data in a global coordinate system.

As shown in step 804 each one of the poses in the sequence of poses may be associated with a previous pose and a next pose by a spatial link such as motion estimation parameters or other camera path information. It should also be understood that while a system may infer camera path from the resulting three-dimensional measurements at each camera position and orientation, the camera path may also, or instead be obtained using a hardware-based positioning system based upon, for example, accelerometers, a geopositioning system, external position sensors, transducers in an articulating arm or any other combination of sensors and techniques suitable for detecting camera position and/or orientation with sufficient accuracy for the intended three-dimensional reconstruction.

This spatial link data reflects the physical camera path in the order in which data was acquired, thus providing a plurality of spatial links that characterize the camera path during a data acquisition process. The sequence of poses may, for example, be made up of key frames (or sequential pairs of key frames) as generally described above, where additional data sets are acquired from one or more additional poses between each sequential pair of key frames. Key frames may be usefully employed, for example, to reduce the computational complexity of path optimization while retaining a contiguous camera path of sequential poses. After path optimization is complete, additional three-dimensional data may be added based upon the one or more additional data sets and the one or more additional poses from between key frames. As described above, key frames may be selected from a larger set of poses using a metric to evaluate a quality of a resulting three-dimensional reconstruction, a quality of the estimated motion parameters between poses, a degree of overlap in scanned subject matter, a graph analysis or any other useful technique or metric.

As shown in step 806, at least one non-sequential spatial link may be identified between two non-sequential ones of the poses based upon the data set for each of the two non-sequential ones of the poses. Thus for example two data sets from a buccal and lingual scan segment may be related to one another based upon camera position, the three-dimensional data recovered from the respective data sets, or any other data acquired during a scanning process. In one aspect, a metric may be employed to identify candidates for non-sequential spatial links, such as a ratio of spatial distance between two data sets to the length of an intervening camera path. Thus the non-sequential spatial link(s) may associate two of the sequence of poses that are separated by a substantially greater distance along the camera path than along the surface of the dental object. This may be based on the data set for each of the two non-sequential ones of the poses, such as by using camera pose data to determine a surface position or by identifying an overlap in the reconstructed three-dimensional data obtained using the data set for two non-sequential poses. This may also include displaying a region for one or more candidate links in a user interface and receiving a supplemental scan of the region, as described above for example with reference to FIG. 5.

As shown in step 808, a global motion optimization may be performed on the camera path to minimize an error among the plurality of spatial links and the at least one non-sequential spatial link, thereby providing an optimized camera path. This may employ, for example, any of the optimization techniques described above. More generally, this may include any technique for minimizing errors in motion estimation parameters expressed as a function of one or more of rotation, translation, coupled rotation and translation, and decoupled rotation and translation, and/or any technique for aligning the three-dimensional data reconstructed from the data sets in a global coordinate system or improving a consistency of the sequence of poses along the camera path in the global coordinate system.

As shown in step 810, a three-dimensional model of the dental object may be reconstructed using known techniques based upon the optimized camera path and the plurality of data sets.

Thus by observing the actual camera paths typical of intra-oral dental scanning, the applicants have devised improved techniques for error minimization when camera path is used for three-dimensional reconstruction. More specifically, by observing that intra-oral scanning often employs a number of adjacent, relatively straight global paths such as for lingual, occlusal, and buccal surfaces (as dictated in part by the relatively restricted oral access to the relatively large surfaces of dentition), and by observing that intra-oral scanning regularly returns to earlier scan positions, the applicants have devised an optimization technique that takes advantage of the spatial relationship between certain non-sequential frames of data. The approach described above solves the problem of conflicting data for local measurements by using an error minimization technique that globally addresses the camera path, including the interrelationship of non-sequential frames of data. This may be particularly useful, for example for scans covering gums, soft tissue, full arches, orthodontic components and the like where scanning a large area typically entails multiple passes over various regions of the scanned surface.

Figure 9:
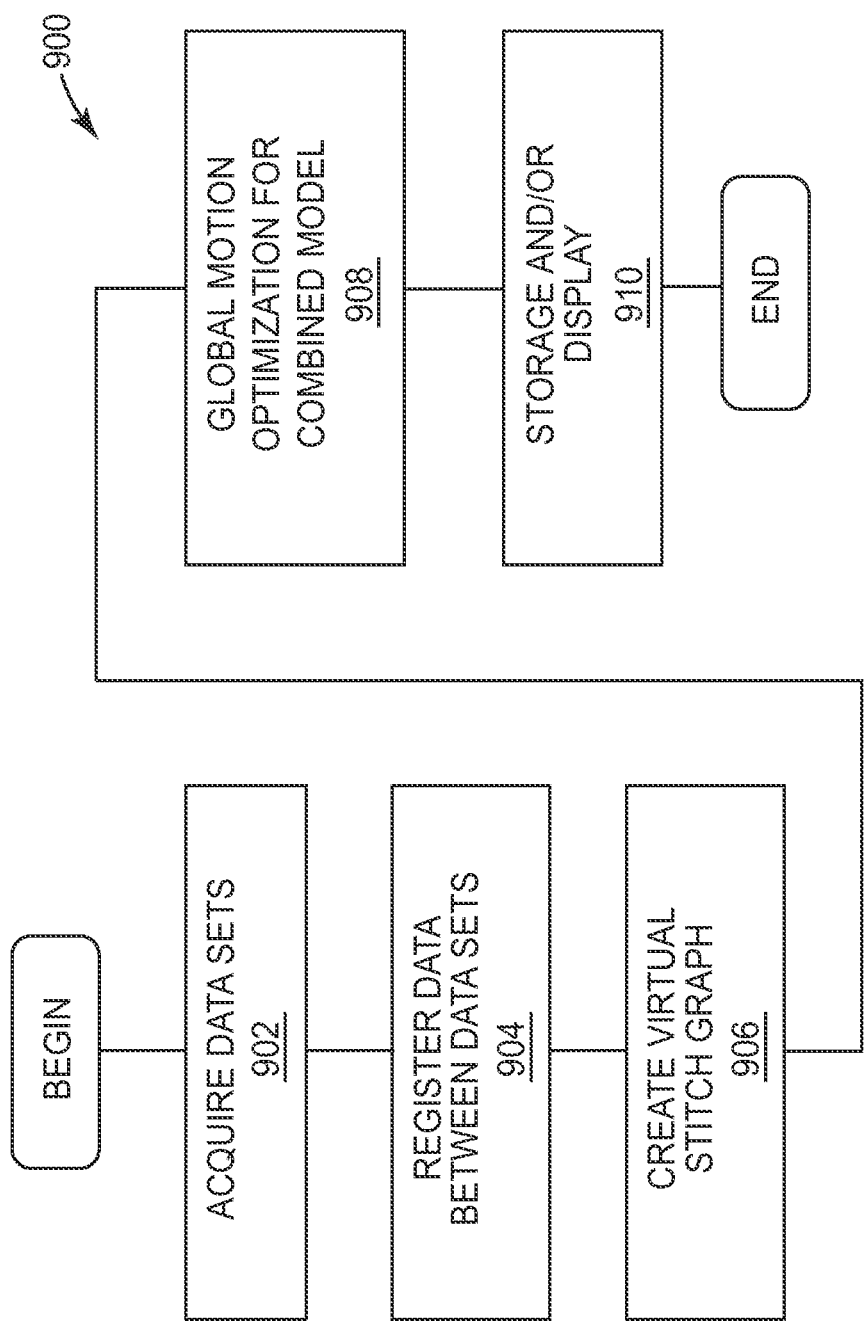
FIG. 9 is a flow chart of a hybrid stitching process for combining disparate three-dimensional scans of a common surface.

FIG. 9 is a flow chart of a hybrid stitching process for combining disparate three-dimensional scans of a common surface. In scanning techniques that use a camera path for reconstruction, the full scan data for an object may include any number of disparate scans with camera paths, or more generally stitch graphs, that are not directly spatially related to one another. The following process 900 provides a technique for establishing spatial relationships between such stitch graphs through a series of local geometry-based registrations. The resulting, combined model may then be subjected to any of the optimization techniques described above as though it had been obtained from a single, continuous scan.

As shown in step 902, the process 900 may begin with obtaining a first three-dimensional model including a first plurality of frames of data, each including sets of three-dimensional points spatially related to one another by a first camera path. It will be understood that a 'camera path' generally refers to a sequential series of poses connected by a number of transforms from one to the next. However, the camera path of the model may more generally include any number of interrelationships or 'stitches' between non-sequential poses that can be inferred from other spatial information such as overlapping regions of an object surface in the accompanying sets of three-dimensional points. In the foregoing description, terms such as camera path and stitch graph should be broadly interpreted to include any rigid transformations and/or other descriptive data that characterizes camera motion (and reliability thereof) in a manner that permits path-based reconstruction of a three-dimensional surface. Step 902 may also include obtaining a second three-dimensional model including a second plurality of frames of data, each including sets of three-dimensional points spatially related one another by a second camera path. The second model may, for example, be obtained after a first scan is automatically or manually interrupted, or after a first scan is completed and additional data is required or desired, either by a user or in response to prompting from a scanning system as contemplated above. More generally, the second three-dimensional model may be any disparate data set that is not directly spatially related to the first three-dimensional model through a single scan or camera path.

As shown in step 904 one of the first plurality of sets of three-dimensional points may be registered to one of the second plurality of sets of three-dimensional points. This registration may use an iterative closest point algorithm, image-based registration or any suitable technique for three-dimensional registration of points and/or surfaces. In one aspect, a surface mesh may be obtained for use in the registration process. Thus a surface mesh of the first and second plurality of sets of three-dimensional points may be generated with a mesh generation algorithm to obtain polygonal surface representations of each model (or portions thereof). This may generally include generating a surface mesh of the entire first and second models, or a known overlapping surface of the first and second data sets, or a neighborhood surrounding a known common surface, or each of the entire first and second models. The resulting first surface mesh and second surface mesh may then be registered to one another using any suitable techniques, resulting in a known, rigid transformation between the first model and the second model (or between the first surface mesh from the first model and the second surface mesh from the second model). As a result of this spatial relationship, the first three-dimensional model and the second three-dimensional model can be placed in a shared coordinate system that permits subsequent processing using data from both models as a combined surface.

As shown in step 906, the process 900 may include creating a virtual stitch graph that spatially relates individual ones of the first plurality of sets and the second plurality of sets using virtual stitches between the data sets, thereby providing a combined model that includes the first plurality of sets and the second plurality of sets all spatially related by the virtual stitch graph. Numerous techniques may be employed for synthesizing a virtual stitch graph to inter-relate the models. The details of one particular approach are provided below with reference to FIG. 10. It will be appreciated that the term 'virtual' as used in this context is intended to distinguish models using data from multiple disparate scans. Thus while the source of data (multiple camera paths) used to calculate 'virtual stitches' and/or virtual stitch graphs may be different from the data (single camera paths) used to calculate other stitches and graphs, the resulting data can advantageously be provided in a form for use interchangeably with and undistinguishable from data derived from a single scan. As such, in a preferred embodiment, there may be little to distinguish a 'virtual' stitch or a virtual stitch graph from those that are not virtual, except perhaps for their absence from the two or more disparate models from which they were derived.

As shown in step 908, the process 900 may include refining the combined model with a global motion optimization of the virtual stitch graph. With a single virtual stitch graph that inter-relates all of the data from each of the disparate sets (acquired from different scans), any of the global motion optimization techniques described above may be suitable employed to minimize errors on a stitch-by-stitch basis among the combined data sets. In one aspect, this optimization includes a deformable registration where, as distinguished from calculating error-minimized rigid transformations, each stitch or step of the camera path can be moved spatially to minimize global error. Thus in one aspect, the process 900 includes refining the combined model with a deformable registration.

As shown in step 910, the combined model may be stored and/or displayed. This may include, for example, displaying the combined model at a chairside scanning location or a dental laboratory. The combined model may also be stored locally at a scanner site, or transmitted to a central repository for project management including, without limitation, billing, quality assurance, and scheduling fabrication of a dental object at a dental laboratory. The original source data from the disparate scans (for example, disparate camera paths, frames of image data, etc.) may be retained for further processing or for evaluation of the combined model, or the source data may be deleted once the combined model is obtained.

Figure 10:
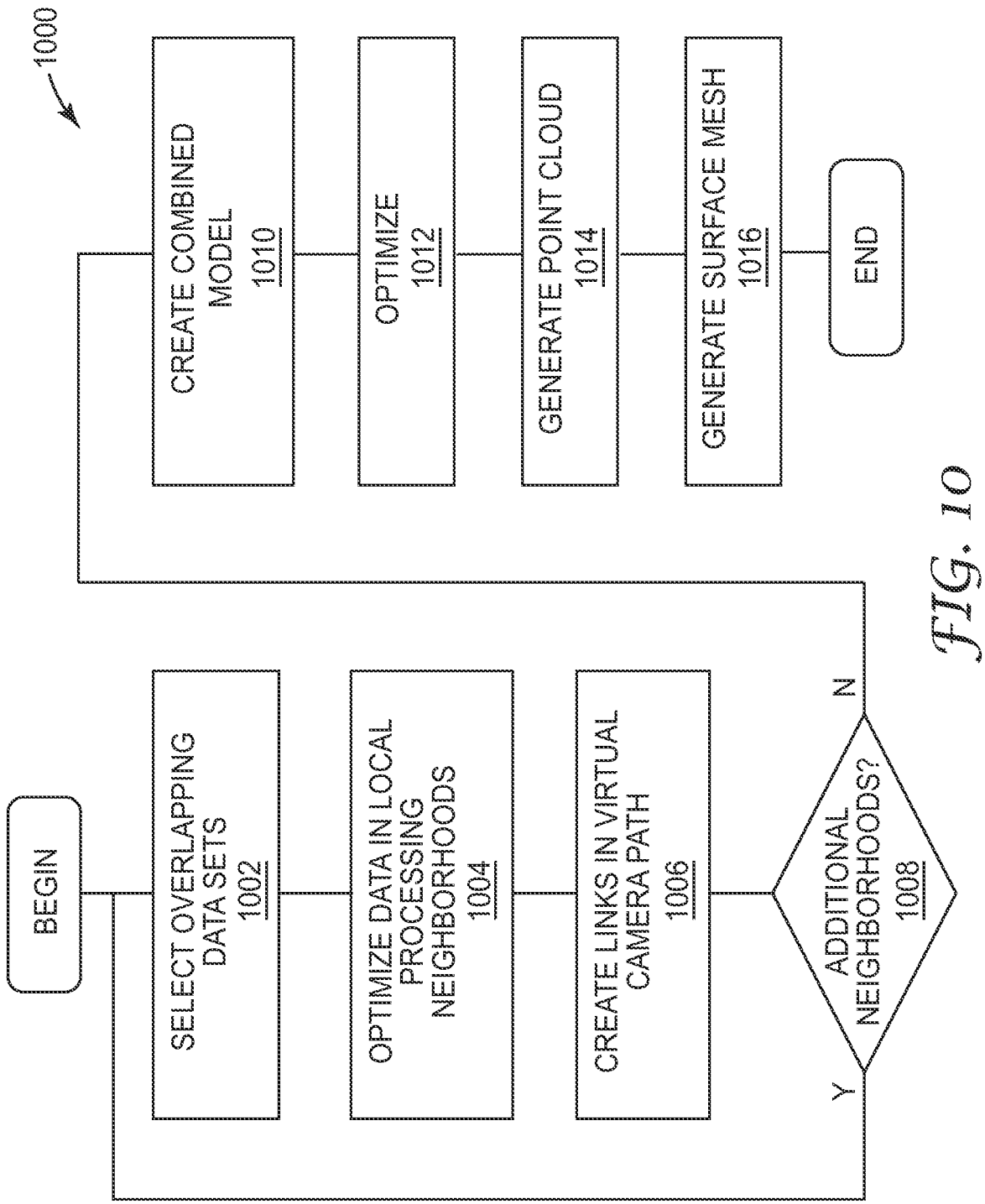
FIG. 10 is a flow chart of a process for creating of a virtual stitch graph.

FIG. 10 is a flow chart of a process for creating of a virtual stitch graph. In the following description, it is assume that two disparate three-dimensional models are provided, each obtained from a sequence of frames of data spatially related by a camera path as generally described above, and that the two models have been registered to establish an initial rigid transformation between them. It will be appreciated that modifications or adaptations of the foregoing may be appropriate where other three-dimensional scanning techniques are employed, or where three or more disparate data sets are concurrently reconciled, all of which is intended to fall within the scope of this disclosure.

As shown in step 1002, the process 1000 may include selecting overlapping data sets. This may, for example, include selecting a first selected one of the first plurality of sets and a second selected one of the second plurality of sets that overlap on the combined surface obtained from the coarse registration described above with reference to FIG. 9. An initial selection of one of the first or second plurality of sets may be, for example, a random selection or a parameterized selection based on, for example, location within the first or second meshes or proximity to a centroid or other feature of interest in the combined or separate surfaces.

All of the frames or sets of data from the first plurality of sets (for example, the first model) in a neighborhood about the first selected one may then also be selected for use as a local processing neighborhood. This may, for example, be all sets of data within a certain number of stitches away, such as all sets within five stitches, or a certain number of steps along a camera path. In order to reduce redundant processing, the sets within this local processing neighborhood may optionally be marked or otherwise identified as unavailable for future processing after the local hybrid stitching operations of the process 1000 are completed. Using the coarse registration of surface meshes, one of the second plurality of sets (for example, a frame from the second model) may be selected that is near (or nearest) to the local processing neighborhood. All of the frames or sets of data from the second plurality of sets in a neighborhood about the second selected one of the second plurality of sets may then be identified in a similar manner to the selection of the local processing neighborhood, for example, by selecting frames or sets of data in the second plurality of sets of data that are within a certain number of stitches or sequential camera poses from the second selected one. It will be appreciated in this context that the use of a stitch graph (of stitches, which may extend in numerous directions from a single camera pose) can provide a significant processing advantage over a camera path (of individual transforms from one camera pose to the next) by affording more options for coverage of relevant regions of a surface of an object.

The selection of local processing neighborhoods for frames from the first and second plurality of data sets may be further refined, such as by restricting or prohibiting use of data sets outside a surface or region common to the two neighborhoods.

As shown in step 1004, data may be optimized in the local processing neighborhoods. For example, where each data set is represented by a camera path or stitch graph that inter-relates sets of three-dimensional points through a sequence of camera poses or the like, a sub-graph of the camera path or stitch graph may be selected for each of the models that only contains data (frames or sets of three-dimensional data points, along with stitches or camera path information) from within the local processing neighborhoods. This approach advantageously removes the influence of data external to the local processing neighborhoods. At this point in the processing, the data still generally comprises two disparate models—in this case, sub-graphs of the full data set—that are associated by a single rigid transform obtained from the coarse registration of surface meshes. This data may be further optimized prior to hybrid stitching by, for example, performing a global motion optimization (as described above) on each of the extracted sub-graphs. With the sub-graphs so optimized, the registration between the two sub-graphs may be refined by repeating an iterative closest point algorithm or other suitable registration process for the two point clouds represented by the optimized sub-graphs. While this approach to optimization is effective in a three-dimensional surface reconstruction based upon camera paths, it will be appreciated that a variety of other optimizations are known in the art for three-dimensional reconstructions, any of which may be adapted to optimization of the local processing neighborhoods contemplated herein.

As shown in step 1006, links for a virtual stitch graph (also referred to as 'hybrid' or 'virtual' stitches) may be created. This may include finding a frame from each of the two sub-graphs closest to a centroid of the overlapping region between the two sub-graphs. These two frames may then be directly spatially related to one another by a rigid transformation, which may be a newly calculated rigid transformation or a refinement of the rigid transformation obtained in the optimization steps described above. Using this transformation, data from the two sub-graphs may be transposed into a common coordinate system, such as the original coordinate system of one of the sub-graphs. This may be repeated for one or more other frames of data in the two sub-graphs to provide a number of direct spatial relationships or 'virtual stitches' between frames in the first sub-graph and frames in the second sub-graph. These relationships may be used directly as stitches in a combined, virtual stitch graph, or further processed as appropriate to express these new relationships in the same form as existing stitches in the stitch graphs or camera paths of the initial models.

In order to facilitate concurrent processing of the actual stitches in the original models and the virtual stitches created for the virtual stitch graph that combines the models, additional characterizing data may be included in each virtual link. For example, a covariance matrix that weights confidence in each link according to multiple degrees of freedom (for example, six degrees of freedom for full translation and rotation) may be provided. While such a covariance matrix results from, for example, the iterative closest point registration process, the use of a particular form is less significant than sufficient commonality between the expression of actual stitches and the virtual stitches for undifferentiated processing of data from both sources in a combined model.

As shown in step 1008, if there are additional neighborhoods of overlapping data to be locally optimized, the process may return to step 1002 where additional overlapping data sets can be selected to create additional virtual links. This may be repeated as often as necessary or desired. If there are no further local neighborhoods for processing, or if some other termination condition such as a threshold number of virtual links or percentage coverage of the full surface area of the combined model has been reached, then the process 1000 may proceed to step 1010.

As shown in step 1010, a combined model may be created that combines the actual stitch graphs from the two original models and the virtual stitches established between the two models as described above. In addition, any number of additional virtual stitches may be added based upon other data in the global models (as distinguished from the local processing neighborhoods), such as nearly identical and/or substantially co-located data sets in the first and second models. In addition, the combined model may be analyzed for completeness and to identify further opportunities for establishing additional stitches between data sets either with or without regard for whether the data sets are from the first model or the second model.

As shown in step 1012, the combined model may be optimized using, for example, global motion optimization as described above to minimize errors in the transformations between related camera poses of the combined model (as distinguished from either of the original stitch graphs or camera paths).

As shown in step 1014, a point cloud may be generated for the combined model that places all of the three-dimensional points of the combined model into a single, common coordinate system.

As shown in step 1016, a surface mesh may be generated for the point cloud using any suitable surface meshing techniques. The model may also be stored, displayed, transmitted or otherwise processed or handled as generally contemplated by the foregoing description.

It will be appreciated that any of the above system and/or methods may be realized in hardware, software, or any combination of these suitable for the data acquisition and modeling technologies described herein. This includes realization in one or more microprocessors, microcontrollers, embedded microcontrollers, programmable digital signal processors or other programmable devices, along with internal and/or external memory. The may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. Thus in one aspect there is disclosed herein a computer program product comprising computer executable code that, when executing on one or more computing devices, performs any and/or all of the steps described above.

At the same time, processing may be distributed across devices such as a camera and/or computer and/or fabrication facility and/or dental laboratory and/or server in a number of ways or all of the functionality may be integrated into a dedicated, standalone device.

In another aspect, a system disclosed herein includes means such as any of the structures described above for performing the functions expressed or implied in the flow charts and other portions of the above description.

All such permutations and combinations that would be apparent to one of ordinary skill in the art are intended to fall within the scope of the present disclosure, which along with the claims is intended to be interpreted in the broadest sense allowable by law.

What is claimed is:
1. A method comprising:
obtaining a first three-dimensional model including a first plurality of sets of three-dimensional points spatially related to one another by a first camera path;
obtaining a second three-dimensional model including a second plurality of sets of three-dimensional points spatially related to one another by a second camera path;
registering one of the first plurality of sets of three-dimensional points to one of the second plurality of sets of three-dimensional points to place the first three-dimen- sional model and the second three-dimensional model in a shared coordinate system;

creating a virtual stitch graph that spatially relates the first plurality of sets and the second plurality of sets, thereby providing a combined model that includes the first plurality of sets and the second plurality of sets all spatially related by the virtual stitch graph; and refining the combined model with a global motion optimization of the virtual stitch graph.

2. The method of claim 1 further comprising generating a first surface mesh of the first three-dimensional model and a second surface mesh of the second three-dimensional model.

3. The method of claim 2 wherein registering includes registering the first surface mesh to the second surface mesh, thereby providing a combined surface.

4. The method of claim 3 wherein registering includes registering with an iterative closest point algorithm.

5. The method of claim 3 further comprising selecting a first selected one of the first plurality of sets and a second selected one of the second plurality of sets that overlap on the combined surface.

6. The method of claim 5 wherein at least one of the first selected one and the second selected one is a set of three-dimensional data closest to a centroid of the combined surface.

7. The method of claim 5 further comprising calculating a rigid transformation and a mean error between the first selected one and the second selected one.

8. The method of claim 7 further comprising selecting a first neighborhood of the first plurality of sets from about the one of the first plurality of sets and a second neighborhood of the second plurality of sets from about the one of the second plurality of sets.

9. The method of claim 8 further comprising:

extracting a sub-region of the combined surface;

spatially relating two or more of the first plurality of sets to two or more of the second plurality of sets within the sub-region to provide a virtual stitch graph; and minimizing an error among spatial relationships in the virtual stitch graph, thereby providing a combined data set for the sub-region.

10. The method of claim 9 further comprising creating at least one virtual stitch between two unstitched ones of the first plurality of sets.

11. The method of claim 1 further comprising refining the combined model with a deformable registration.

12. A computer program product comprising computer executable code embodied on a non-transitory computer readable medium that, when executing on one or more computing devices, performs the steps of:

obtaining a first three-dimensional model including a first plurality of sets of three-dimensional points spatially related to one another by a first camera path;

obtaining a second three-dimensional model including a second plurality of sets of three-dimensional points spatially related to one another by a second camera path;

registering one of the first plurality of sets of three-dimensional points to one of the second plurality of sets of three-dimensional points to place the first three-dimensional model and the second three-dimensional model in a shared coordinate system;

creating a virtual stitch graph that spatially relates the first plurality of sets and the second plurality of sets, thereby providing a combined model that includes the first plurality of sets and the second plurality of sets all spatially related by the virtual stitch graph; and refining the combined model with a global motion optimization of the virtual stitch graph.

13. The computer program product of claim 12 further comprising code that performs the step of generating a first surface mesh of the first three-dimensional model and a second surface mesh of the second three-dimensional model.

14. The computer program product of claim 13 wherein registering includes registering the first surface mesh to the second surface mesh, thereby providing a combined surface.

15. The computer program product of claim 14 wherein registering includes registering with an iterative closest point algorithm.

16. The computer program product of claim 14 further comprising code that performs the step of selecting a first selected one of the first plurality of sets and a second selected one of the second plurality of sets that overlap on the combined surface.

17. The computer program product of claim 16 wherein at least one of the first selected one and the second selected one is a set of three-dimensional data closest to a centroid of the combined surface.

18. The computer program product of claim 16 further comprising code that performs the step of calculating a rigid transformation and a mean error between the first selected one and the second selected one.

19. The computer program product of claim 18 further comprising code that performs the step of selecting a first neighborhood of the first plurality of sets from about the one of the first plurality of sets and a second neighborhood of the second plurality of sets from about the one of the second plurality of sets.

20. The computer program product of claim 19 further comprising code that performs the steps of:

extracting a sub-region of the combined surface;

spatially relating two or more of the first plurality of sets to two or more of the second plurality of sets within the sub-region to provide a virtual stitch graph; and minimizing an error among spatial relationships in the virtual stitch graph, thereby providing a combined data set for the sub-region.

21. The computer program product of claim 20 further comprising code that performs the step of creating at least one virtual stitch between two unstitched ones of the first plurality of sets.

22. The computer program product of claim 12 further comprising code that performs the step of refining the combined model with a deformable registration.

23. A system comprising:

a scanner configured to obtain a first three-dimensional model including a first plurality of sets of three-dimensional points spatially related to one another by a first camera path and a second three-dimensional model including a second plurality of sets of three-dimensional points spatially related with one another by a second camera path;

a processor and memory configured to register one of the first plurality of sets of three-dimensional points to one of the second plurality of sets of three-dimensional points to place the first three-dimensional model and the second three-dimensional model in a shared coordinate system, to create a virtual stitch graph that spatially relates the first plurality of sets and the second plurality of sets, thereby providing a combined model that includes the first plurality of sets and the second plurality of sets all spatially related by the virtual stitch graph, and to refine the combined model with a global motion optimization of the virtual stitch graph; and a display configured to render the combined model.

24. A system comprising:

scanning means for obtaining a first three-dimensional model including a first plurality of sets of three-dimensional points spatially related to one another by a first camera path and a second three-dimensional model including a second plurality of sets of three-dimensional points spatially related with one another by a second camera path; and processing means for registering one of the first plurality of sets of three-dimensional points to one of the second plurality of sets of three-dimensional points to place the first three-dimensional model and the second three-dimensional model in a shared coordinate system, creating a virtual stitch graph that spatially relates the first plurality of sets and the second plurality of sets, thereby providing a combined model that includes the first plurality of sets and the second plurality of sets all spatially related by the virtual stitch graph, and refining the combined model with a global motion optimization of the virtual stitch graph.

* * * * *